United States Patent [19]

Mine et al.

[11] Patent Number: 5,856,562
[45] Date of Patent: Jan. 5, 1999

[54] METHOD FOR INHIBITING POLYMERIZATION OF (METH) ACRYLIC ACID OR ESTERS THEREOF

[75] Inventors: Norioki Mine; Tooru Segi, both of Yokkaichi, Japan

[73] Assignee: Mitsubishi Chemical Corporation, Tokyo-to, Japan

[21] Appl. No.: 863,192

[22] Filed: May 27, 1997

[30] Foreign Application Priority Data

May 27, 1996 [JP] Japan ................................. 8-131766
Dec. 16, 1996 [JP] Japan ................................. 8-352604

[51] Int. Cl.⁶ .................................................. C07C 69/52
[52] U.S. Cl. ........................................... 560/205; 562/598
[58] Field of Search ............................. 560/205; 562/598

[56] References Cited

U.S. PATENT DOCUMENTS 3,818,079 6/1974 Sato et al. .
4,127,603 11/1978 Bljimberg et al. .
5,504,243 4/1996 Sakamoto et al. .

FOREIGN PATENT DOCUMENTS 2 285 983 8/1995 United Kingdom .

*Primary Examiner*—Paul J. Killos
*Attorney, Agent, or Firm*—Oblon, Spivak, McClelland, Maier & Neustadt, P.C.

[57] ABSTRACT

In a method for inhibiting the polymerization of (meth) acrylic acid or esters thereof, the improvement comprising using as a polymerization inhibitor a N-oxyl compound represented by the general formula (1):

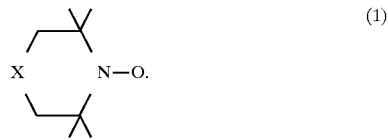

wherein X represents $CH_2$, CHOH, C=O, $CHCOCH_3$ or $CHNHCOCH_2$, in combination with phosphine compound or a cobalt compound.

8 Claims, No Drawings

METHOD FOR INHIBITING POLYMERIZATION OF (METH) ACRYLIC ACID OR ESTERS THEREOF

BACKGROUND OF THE INVENTION

1. Field of the Invention

The present invention relates to a method for inhibiting the polymerization of acrylic or methacrylic acid (acrylic acid and methacrylic acid being hereinafter collectively referred to as "(meth)acrylic acid") or esters thereof. More particularly, the present invention relates to a method for effectively inhibiting the polymerization of (meth)acrylic acid or esters thereof during their storage or upon their preparation, e.g., at a distillation stage.

2. Background Art (Meth)acrylic acid or esters thereof have widely been utilized as raw materials for organic polymeric materials and a variety of organic materials. With the recent expansion of the field in which (meth)acrylic acid or esters thereof are utilized, those ones which have higher purities have been demanded. (Meth)acrylic acid and esters thereof tend to be naturally polymerized by light or heat. Therefore, there have been proposed to use various polymerization inhibitors in order to inhibit such a natural polymerization of (meth)acrylic acid or esters thereof during their storage or preparation. For instance, British Patent No. 1,127,127 discloses that an N-oxy radical such as tert-butylnitroxide or 2,2,6,6-tetramethyl-4-hydroxy-piperidine-1-oxyl, when used as a stabilizer for acrylic acid, exhibits a better polymerization-inhibiting effect than conventionally-known hydroquinone, phenothiazine and copper (II) chloride.

Further, U.S. Pat. No. 4,127,603 discloses a method for inhibiting the polymerization of methacrylic acid, in which 2,2,6,6-tetramethyl-4-hydroxypiperidine-1-oxyl or 2,2,6,6-tetramethylpiperidine-1-oxyl is allowed to exist in the catalytic oxidation reaction of methacrolein to produce methacrylic acid; and Japanese Patent Publication No. 46, 496/1983 discloses a method for inhibiting the polymerization of (meth)acrylic acid esters, using an N-oxyl compound such as 2,2,5,5-tetramethyl-3-oxopyrrolidine-1-oxyl or 2,2,6,6-tetramethyl-4-acetoxypiperidine-1-oxyl.

Furthermore, European Patent Publication No. 620,206 discloses the use of 2,2,6,6-tetramethylpiperidine-1-oxyl, hydroquinone and phenothiazine in combination for inhibiting the polymerization of (meth)acrylic acid or esters thereof; and U.S. Pat. No. 5,504,243 teaches the polymerization-inhibiting effect which can be attained when an N-oxyl compound such as 2,2,6,6-tetramethyl-4-hydroxy-piperidine-1-oxyl is used in combination with other compounds such as manganese salt compounds, copper salt compounds, 2,2,6,6-tetramethylpiperidine compounds or nitroso compounds. In addition, British Patent Publication No. 2,285,983 discloses the use of phenothiazine, hydroquinone or the like in combination with copper dithiocarbamate, and metallic cobalt, cobalt oxide, cobalt acetate or the like, as a polymerization inhibitor for acrylic acid during its distillation process.

However, the above-described conventional methods for inhibiting the polymerization of (meth)acrylic acid or esters thereof have the problem that the polymerization is not always fully inhibited depending upon the conditions under which these methods are applied, especially under the high-temperature conditions upon the distillation of (meth)acrylic acid or esters thereof.

SUMMARY OF THE INVENTION

An object of the present invention is therefore to overcome the drawback in the prior art and provide a method for inhibiting the polymerization of (meth)acrylic acid or esters thereof, which can effectively inhibit the polymerization even under the high-temperature conditions during the distillation of the (meth)acrylic acid or ester thereof, and thus enables a long-term stable operation of the plant.

It has now been found by the present inventors that the above object can be attained by the use as a polymerization inhibitor of an N-oxyl compound in combination with a specific compound.

Thus, the present invention provides in a method for inhibiting the polymerization of (meth)acrylic acid or esters thereof, the improvement comprising using as a polymerization inhibitor an N-oxyl compound represented by the general formula (1):

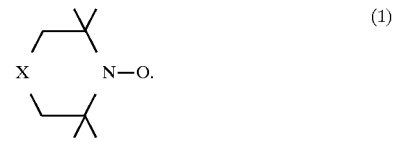

wherein X represents $CH_2$, $CHOH$, $C=O$, $CHCOCH_3$ or $CHNHCOCH_3$, in combination with a phosphine compound or a cobalt compound.

The method of the present invention, due to the use of the specific polymerization inhibitor which has a remarkably higher polymerization-inhibiting effect than the conventional polymerization inhibitors, can effectively prevent the occurrence of polymerization of (meth)acrylic acid or esters thereof even during a high-temperature distillation stage in their preparation, let alone during their storage.

DETAILED DESCRIPTION OF THE INVENTION

The objects of the polymerization inhibition to which the present invention is directed are (meth)acrylic acid and esters thereof. Examples of the (meth)acrylic acid esters include alkyl esters, such as methyl, ethyl, propyl, butyl and 2-ethylhexyl esters, of (meth)acrylic acid. Substituted alkyl esters of (meth)acrylic acid such as 2-hydroxyethyl and 2-hydroxypropyl esters of (meth)acrylic acid can also be used.

One polymerization inhibitor component for use in the method of the present invention is an N-oxyl compound represented by the above general formula (1). Preferable examples of such a compound include 2,2,6,6-tetramethyl-piperidine-1-oxyl, 2,2,6,6-tetramethyl-4-hydroxypiperidine-1-oxyl and 2,2,6,6-tetramethyl-4-oxopiperidine-1-oxyl. These compounds can be used singly; or at least two of these compounds can be used in combination.

The amount of the N-oxyl compound to be used varies depending upon the type of the N-oxyl compound used, the type of the (meth)acrylic acid or ester thereof to be treated, or the conditions under which the N-oxyl compound is used, such as temperature. However, it is generally selected from the range of 5 to 1,000 ppm, preferably from the range of 50 to 500 ppm by weight of the (meth)acrylic acid or ester thereof to be treated.

The other polymerization inhibitor component for use in the method of the present invention is either a phosphine compound or a cobalt compound.

A compound represented by the general formula (2):

wherein R, R' and R" each independently represent an alkyl group having 1 to 10 carbon atoms, or an aryl group having 6 to 10 carbon atoms, can be used as the phosphine compound.

Specific examples of the phosphine compound include trimethylphosphine, triethylphosphine, tri-n-propylphosphine, tri-i-propylphosphine, tri-n-butylphosphine, tri-i-butyl-phosphine, triphenylphosphine, dimethylphenylphosphine and methyldiphenylphosphine. Of these, triphenylphosphine and tri-n-butylphosphine are preferred.

These phosphine compounds can be used either singly or in combination.

The amount of the phosphine compound to be used is selected generally from 10 to 5,000 ppm, preferably from 50 to 1,000 ppm by weight of the (meth)acrylic acid or (meth) acrylic acid ester to be treated.

As the cobalt compound, an inorganic acid salt of cobalt such as cobalt carbonate, cobalt nitrate or cobalt sulfate, an aliphatic or aromatic carboxylic acid salt of cobalt such as cobalt acetate, cobalt propionate, cobalt decanoate, cobalt terephthalate or cobalt (meth)acrylate, a cobalt halide such as cobalt chloride or cobalt bromide, or cobalt hydroxide can be used. Preferable cobalt compounds are cobalt carboxylates, especially cobalt acetate and cobalt propionate. The above-enumerated cobalt compounds can be used either singly or in combination.

The amount of the cobalt compound to be used can vary depending upon the type of the cobalt compound used, the type of the (meth)acrylic acid or ester thereof to be treated, or the conditions under which the cobalt compound is used. However, it is generally selected from the range of 10 to 5,000 ppm, preferably from the range of 50 to 1,000 ppm by weight of the (meth)acrylic acid or ester thereof to be treated.

As the polymerization inhibitors for use in the method of the present invention, it is preferable to use 2,2,6,6-tetramethylpiperidine-1-oxyl or 2,2,6,6-tetramethyl-4-hydroxypiperidine-1-oxyl as the above-described N-oxyl compound, and cobalt acetate or cobalt carbonate as the cobalt compound. A combination of 2,2,6,6-tetramethylpiperidine-1-oxyl and cobalt acetate is particularly preferred in the light of polymerization-inhibiting effect.

Conventional polymerization inhibitors can also be used together with the above-described polymerization inhibitor as long as they do not impair the intended polymerization-inhibiting effect. Specifically, the use of the polymerization inhibitor of the present invention together with hydroquinone, methoxyquinone, diphenylamine, phenylenediamine or the like can reduce the amount of the N-oxyl compound to be used, as the case may be.

However, phenothiazine, copper acetate, copper dialkyldithiocarbamate, 2,2,6,6-tetramethyl-4-hydroxypiperidine and the like are incompatible especially with the N-oxyl compound, and if one of these compounds is used along with the polymerization inhibitors of the present invention, the polymerization of (meth)acrylic acid or esters thereof tends to be promoted.

The polymerization inhibitor for use in the method of the present invention can be used in any form, and they can be added in the same form as in the case of conventional polymerization inhibitors. Namely, each polymerization inhibitor component can be directly added in the form of a solid or powder, or can be added as a solution in an organic solvent. Moreover, there is no particular limitation on the manner of the addition of the polymerization inhibitor: the polymerization inhibitor can be added separately, or they can be added simultaneously, for example, in the form of a solution thereof.

Furthermore, the method of the present invention can be applied at any point in order to inhibit the polymerization of (meth)acrylic acid or esters thereof. Although it is possible to apply the method when (meth)acrylic acid or esters thereof are stored or transported, it is more effective to apply the method to the process of the separation/purification of (meth)acrylic acid or esters thereof, conducted by means of distillation at high temperatures. Specifically, the polymerization of, for instance, acrylic acid can be inhibited by allowing the polymerization inhibitor of the invention to properly exist in an apparatus for use in each of such distillation/ separation processes as the azeotropic separation of an aqueous crude acrylic acid solution obtained from the gas phase catalytic oxidation reaction of propylene, the separation between acrylic acid and low-boiling materials, and the rectification of acrylic acid. For instance, it is possible to inhibit the polymerization by introducing the polymerization inhibitor, which has been added in the feed or reflux, to an apparatus for use in each process; or the polymerization inhibitor can be fed from the top of a distillation column to inhibit the polymerization in a gas phase.

When the method of the present invention is employed, an adequate polymerization-inhibiting effect can be achieved either in the presence of or in the absence of molecular oxygen. In this connection, it is usual with the conventional methods to utilize molecular oxygen together with a polymerization inhibitor to enhance the polymerization-inhibiting effect. In contrast, the method of the present invention, due to the use of the specific polymerization inhibitor having a sufficiently high polymerization-inhibiting effect, can avoid the need for the use of molecular oxygen. Thus, the method of the present invention makes it possible to treat readily polymerizable (meth)acrylic acid or its esters in various gaseous atmospheres ranging from the air to an atmosphere containing no oxygen, such as nitrogen atmosphere.

The following examples further illustrate the present invention but are not intended to limit it.

EXAMPLE 1

Azeotropic separation of an aqueous solution of acrylic acid was conducted by using a packed column in which a 500 ml glass flask was used as the bottom of the column, the top of the column was equipped with a pipe for distillate, and the central part of the column was equipped with a feed pipe, in the following manner: A model of a product which is obtainable by allowing water to absorb crude acrylic acid obtained by the gas phase catalytic oxidation reaction of propylene was prepared, and used as a feed. The feed had the following composition: acrylic acid 51.5 wt. %; acetic acid 2.5 wt. %; and water 46.0 wt. %. To this feed were added, as polymerization inhibitors, 2,2,6,6-tetramethyl-piperidine-1-oxyl and triphenylphosphine in amounts of 150 ppm and 300 ppm by weight of the acrylic acid, respectively. This liquid feed was fed to the distillation column at a rate of 270 ml/hour. Distillation was carried out by circulating toluene, an entrainer, as reflux. The operation conditions were as follows: the temperature at the bottom of the column was 90° C., and the temperature and pressure at the top of the column were 50° C. and 180 Torr, respectively. Air was fed to the column through a capillary from the bottom of the column at a rate of 300 N-ml/hour (0.15% by volume). The liquid discharged from the bottom of the column after the system reached to the steady state was found to have the following composition: acrylic acid 89.7 wt. %; acetic acid 3.7 wt. %; water 0.3 wt. %; and toluene 6.3 wt. %. During an operating time of 8 hours, no polymer was produced in the column.

EXAMPLE 2

The procedure of Example 1 was repeated except that 2,2,6,6-tetramethyl-4-hydroxypiperidine-1-oxyl and triphenylphosphine were added as the polymerization inhibitors in amounts of 200 ppm and 300 ppm, respectively. As a result, no polymer was found to be produced except that a polymer-like material was slightly formed in the flask at the bottom of the column.

EXAMPLE 3

The procedure of Example 1 was repeated except that 2,2,6,6-tetramethylpiperidine-1-oxyl, triphenylphosphine and hydroquinone were used as the polymerization inhibitors in amounts of 100 ppm, 300 ppm and 800 ppm, respectively. As a result, no polymer was found to be produced.

EXAMPLE 4

The procedure of Example 1 was repeated except that 2,2,6,6-tetramethylpiperidine-1-oxyl and cobalt (II) acetate were used as the polymerization inhibitors in amounts of 150 ppm and 100 ppm by weight of the acrylic acid, respectively. As a result, no polymer was found to be produced in the column.

EXAMPLE 5

The procedure of Example 1 was repeated except that 2,2,6,6-tetramethyl-4-hydroxypiperidine-1-oxyl and cobalt (II) acetate were used as the polymerization inhibitors in amounts of 200 ppm and 100 ppm, respectively. As a result, no polymer was found to be produced except that a polymer-like material was slightly formed in the flask at the bottom of the column.

EXAMPLE 6

The procedure of Example 1 was repeated except that 2,2,6,6-tetramethylpiperidine-1-oxyl and cobalt carbonate were used as the polymerization inhibitors in amounts of 150 ppm and 300 ppm, respectively. As a result, no polymer was found to be produced.

EXAMPLE 7

The procedure of Example 1 was repeated except that 2,2,6,6-tetramethylpiperidine-1-oxyl, cobalt (II) acetate and hydroquinone were added as the polymerization inhibitors in amounts of 100 ppm, 300ppm and 800 ppm, respectively. As a result, no polymer was found to be produced.

EXAMPLE 8

The procedure of Example 4 was repeated except that nitrogen was fed, instead of the air, from the bottom of the column. As a result, no polymer was found to be produced.

COMPARATIVE EXAMPLE 1

The procedure of Example 1 was repeated except that only 2,2,6,6-tetramethylpiperidine-1-oxyl was used as the polymerization inhibitor in an amount of 150 ppm. As a result, a small amount of a polymer was found in the region from the packing to the neck of the flask.

COMPARATIVE EXAMPLE 2

The procedure of Example 1 was repeated except that only triphenylphosphine was used as the polymerization inhibitor in an amount of 300 ppm. As a result, a considerable amount of a polymer was found in the region from the packing to the neck of the flask.

COMPARATIVE EXAMPLE 3

The procedure of Example 1 was repeated except that 2,2,6,6-tetramethylpiperidine-1-oxyl and phenothiazine were added as the polymerization inhibitors in amounts of 150 ppm and 300 ppm, respectively. As a result, after 3 hours from the initiation of the operation, the column got clogged with the polymer produced, whereby it became impossible to continue the operation.

COMPARATIVE EXAMPLE 4

The procedure of Example 1 was repeated except that 2,2,6,6-tetramethyl-4-hydroxypiperidine-1-oxyl and phenothiazine were added as the polymerization inhibitors in amounts of 150 ppm and 300 ppm, respectively. As a result, a large amount of a polymer was found in the region from the packing to the neck of the flask.

COMPARATIVE EXAMPLE 5

The procedure of Example 1 was repeated except that 2,2,6,6-tetramethyl-4-hydroxypiperidine-1-oxyl and 2,2,6,6-tetramethylpiperidine were added as the polymerization inhibitors in amounts of 150 ppm and 300 ppm, respectively. As a result, within 1 hour from the initiation of the operation, a large amount of a popcorn polymer was produced in the column, and it became impossible to continue the operation.

COMPARATIVE EXAMPLE 6

The procedure of Example 1 was repeated except that phenothiazine and hydroquinone were added as the polymerization inhibitors in amounts of 300 ppm and 800 ppm, respectively. As a result, a considerable amount of a polymer was found in the region from the packing to the neck of the flask.

COMPARATIVE EXAMPLE 7

The procedure of Example 1 was repeated except that 2,2,6,6-tetramethyl-4-hydroxypiperidine-1-oxyl and copper acetate were added as the polymerization inhibitors in amounts of 150 ppm and 300 ppm, respectively. As a result, a considerable amount of a polymer was found in the region from the packing to the neck of the flask.

What is claimed is:

1. In a method for inhibiting the polymerization of (meth) acrylic acid or esters thereof, the improvement comprising using as a polymerization inhibitor an N-oxyl compound represented by the general formula (1):

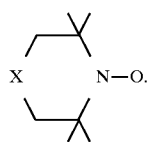
(1)

wherein X represents $CH_2$, CHOH, C=O, $CHCOCH_3$ or $CHNHCOCH_3$, in combination with a phosphine compound or a cobalt compound.

2. The method according to claim 1, wherein the N-oxyl compound is at least one compound selected from the group consisting of 2,2,6,6-tetramethylpiperidine-1-oxyl, 2,2,6,6-tetramethyl-4-hydroxypiperidine-1-oxyl and 2,2,6,6-tetramethyl-4-oxopiperidine-1-oxyl.

3. The method according to claim 1, wherein the phosphine compound is represented by the general formula (2):

(2)

wherein R, R' and R" each independently represent an alkyl group having 1 to 10 carbon atoms, or an aryl group having 6 to 10 carbon atoms.

4. The method according to claim 3, wherein the phosphine compound is triphenylphosphine.

5. The method according to claim 1, wherein the cobalt compound is at least one compound selected from the group consisting of cobalt carbonate, aliphatic or aromatic carboxylic acid salts of cobalt and cobalt hydroxide.

6. The method according to claim 5, wherein the cobalt compound is an aliphatic carboxylic acid salt of cobalt.

7. The method according to claim 1, wherein a solution containing (meth) acrylic acid or esters thereof is subjected to distillation in the presence of said polymerization inhibitor.

8. The method according to claim 7, wherein molecular oxygen is also allowed to exist as a polymerization inhibitor in the distillation system.

* * * * *